(12) United States Patent
Thompson et al.

(10) Patent No.: US 10,821,123 B2
(45) Date of Patent: Nov. 3, 2020

(54) USE OF RIBOSE FOR TREATMENT OF SUBJECTS HAVING CONGESTIVE HEART FAILURE

(71) Applicant: Bioenergy Life Science, Inc., Ham Lake, MN (US)

(72) Inventors: Jeffrey A. Thompson, Shorewood, MN (US); Raj Khankari, Maple Grove, MN (US)

(73) Assignee: Bioenergy Life Science, Inc., Ham Lake, MN (US)

(*) Notice: Subject to any disclaimer, the term of this patent is extended or adjusted under 35 U.S.C. 154(b) by 0 days.

(21) Appl. No.: 15/409,735

(22) Filed: Jan. 19, 2017

(65) Prior Publication Data

US 2017/0216330 A1 Aug. 3, 2017

Related U.S. Application Data

(60) Provisional application No. 62/289,562, filed on Feb. 1, 2016.

(51) Int. Cl.
*A61K 31/7004* (2006.01)
*A61K 9/00* (2006.01)

(52) U.S. Cl.
CPC ........ *A61K 31/7004* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 4,605,644 A | 8/1986 | Foker | |
| 4,719,201 A | 1/1988 | Foker | |
| 4,824,660 A | 4/1989 | Angello et al. | |
| 4,871,718 A | 10/1989 | Carniglia | |
| 4,920,098 A | 4/1990 | Cotter et al. | |
| 4,968,719 A | 11/1990 | Brevetti | |
| 5,114,723 A | 5/1992 | Stray-Gundersen | |
| 5,217,997 A | 6/1993 | Levere et al. | |
| 5,292,538 A | 3/1994 | Paul et al. | |
| 5,391,550 A | 2/1995 | Carniglia et al. | |
| 5,658,889 A * | 8/1997 | Gruber | A61K 31/00 514/43 |
| 5,707,971 A | 1/1998 | Fahy | |
| 5,714,515 A | 2/1998 | Bunger | |
| 5,804,596 A | 9/1998 | Majeed et al. | |
| 6,001,878 A | 12/1999 | Van Leeuwen et al. | |
| 6,051,236 A | 4/2000 | Portman | |
| 6,054,128 A | 4/2000 | Wakat | |
| 6,159,942 A | 12/2000 | St. Cyr et al. | |
| 6,159,943 A | 12/2000 | Butler et al. | |
| 6,172,114 B1 | 1/2001 | McCabe | |
| 6,218,366 B1 | 4/2001 | St. Cyr et al. | |
| 6,339,716 B1 | 1/2002 | Sawada et al. | |
| 6,420,342 B1 | 7/2002 | Hageman et al. | |
| 6,429,198 B1 | 8/2002 | St. Cyr et al. | |
| 6,511,964 B2 | 1/2003 | Butler et al. | |
| 6,525,027 B2 | 2/2003 | Vazquez et al. | |
| 6,534,480 B2 | 3/2003 | Cyr et al. | |
| 6,548,483 B2 | 4/2003 | Hageman et al. | |
| 6,663,859 B2 | 12/2003 | Percival et al. | |
| 6,703,370 B1 | 3/2004 | Butler et al. | |
| 7,094,762 B2 | 8/2006 | Butler et al. | |
| 7,553,817 B2 | 6/2009 | Butler et al. | |
| 8,101,581 B2 | 1/2012 | Herrick | |
| 8,710,018 B2 | 4/2014 | Foker | |
| 8,835,396 B2 | 9/2014 | Verlaan et al. | |
| 9,572,882 B2 | 2/2017 | Butler et al. | |
| 2002/0119933 A1 | 8/2002 | Butler et al. | |
| 2003/0212006 A1 | 11/2003 | Seifert et al. | |
| 2005/0277598 A1 | 12/2005 | MacCarter et al. | |
| 2007/0105787 A1 | 5/2007 | St. Cyr et al. | |
| 2008/0146514 A1 | 6/2008 | Verlaan et al. | |
| 2008/0176809 A1 | 7/2008 | Herrick | |
| 2009/0197818 A1 | 8/2009 | St. Cyr et al. | |
| 2009/0286750 A1 | 11/2009 | Kasubick et al. | |
| 2010/0055206 A1 | 3/2010 | St. Cyr et al. | |

(Continued)

FOREIGN PATENT DOCUMENTS

| | | |
|---|---|---|
| DE | 42 28 215 A1 | 3/1994 |
| EP | 0 312 249 A1 | 4/1989 |
| EP | 0 573 466 B1 | 11/1995 |

(Continued)

OTHER PUBLICATIONS

Held, C. M. D. P., Gerstein, H. C., Yusuf, S., Zhao, F., Hilbrich, L., Anderson, C., . . . & Teo, K. (2007). Glucose levels predict hospitalization for congestive heart failure in patients at high cardiovascular risk. Circulation, 115(11), 1371-1375. (Year: 2007).*
Greenberg, B. (2012). Acute decompensated heart failure. Circulation Journal, 76(3), 532-543. (Year: 2012).*
Joseph, Susan M et al. "Acute decompensated heart failure: contemporary medical management." Texas Heart Institute journal vol. 36,6 (2009): 510-20. (Year: 2009).*
Angello et al., "Recovery of Myocardial Function and Thallium 201 Redistribution Using Ribose," *American Journal of Cardiac Imaging*, Dec. 1989;3(4):256-265.
Bayram et al., "D-Ribose aids heart failure patients with preserved ejection fraction and diastolic dysfunction: a pilot study," Jan. 1, 2015, *Therapeutic Advances in Cardiovascular Disease*, 9(3):56-65.

(Continued)

*Primary Examiner* — Dale R Miller
(74) *Attorney, Agent, or Firm* — Thomas J. Oppold; Larkin Hoffman Daly & Lindgren Ltd.

(57) ABSTRACT

A method for treating a human subject having congestive heart failure is disclosed herein. An exemplary method includes orally administering a 10 g to 50 g dose of D-ribose daily to a subject having congestive heart failure, wherein the D-ribose is administered in a single dose after fasting, and the administration of D-ribose is continued over a period of time effective to improve cardiac and/or physical function of the subject.

20 Claims, 1 Drawing Sheet

(56) References Cited

U.S. PATENT DOCUMENTS

| | | | |
|---|---|---|---|
| 2010/0099630 A1 | 4/2010 | MacCarter et al. | |
| 2011/0053869 A1 | 3/2011 | Foker | |

FOREIGN PATENT DOCUMENTS

| | | |
|---|---|---|
| EP | 0 680 945 A2 | 11/1995 |
| JP | 02286620 A | 11/1990 |
| WO | WO 94/02127 A1 | 2/1994 |
| WO | WO 94/004158 A1 | 3/1994 |
| WO | WO 96/18313 A1 | 6/1996 |

OTHER PUBLICATIONS

Bianco, "How Congestive Heart Failure Works," [retrieved on Sep. 29, 2009}. Retrieved from the Internet:<URL:http://health.howstuffwords.com/congestive-hear.htm/printable; 6 pgs.

Ceremuzyfiski et al., "Effect of Supplemental Oral L-Arginine on Exercise Capacity in Patients With Stable Angina Pectoris," *Am. J. Cardiol.*, Aug. 1, 1997;80:331-333.

Cohn, "Preventing Congestive Heart Failure," *American Family Physician*, Apr. 15, 1998;57(8).

Foker et al., "Adenosine metabolism and myocardial preservation. Consequences of adenosine catabolism on myocardial high-energy compounds and tissue blood flow," *J. Thorac. Cardiovasc. Surg.*, Oct. 1980;80(4):506-516.

Gross et al., "Metabolism of D-Ribose Administered Continuously to Healthy Persons and to Patients with Myoadenylate Deaminase Deficiency," *Klin. Woschenschr.*, 1989;67:1205-1213.

Gross et al., "Ribose Administration during Exercise: Effects on Substrates and Products of Energy Metabolism in Healthy Subjects and a Patient with Myoadenylate Deaminase Deficiency," *Klin. Wochenshr.*, 1991;69:151-155.

International Patent Application No. PCT/US2017/014034, filed Jan. 19, 2017; International Search Report / Written Opinion dated Apr. 11, 2017; 14 pages.

Katz, "Is the failing heart energy depleted?" Nov. 1998, *Cardiol Clinics*, 16(4):633-44.

Konstam et al., "Effects of oral tolvaptan in patients hospitalized for worsening heart failure: The Everest Outcome Trial," Mar. 28, 2007, *JAMA*, 297(12):1319-31.

Konstam et al., "Therapeutic options for patients with, or at risk for, heart failure. In Heart Failure: Pathophysiology, Molecular Biology and Clinical Management," (AM Katz and MA Konstam, Eds) 2009, Lippincott Williams & Wilkins (Philadelphia).

Loscalzo et al., "Nitric oxide and its role in the cardiovascular system," *Prog. Cardiovasc. Dis.*, Sep.-Oct. 1995;38(2):87-104.

MacCarter et al., "D-Ribose aids advanced ischemic heart failure patients," Letters to the Editor, Aurora Denver Cardiology Association, P.C., Denver CO; Elsevier Ireland Ltd., 2008, available online Jul. 31, 2008:79-80.

Mahoney et al., "A Comparison of Different Carbohydrates as Substrates for the Isolated Working Heart," *J. Surg. Res.*, Dec. 1989;47(6):530-534.

Monograph for Corvalen (D-Ribose). Bioenergy Life Science, Inc. Jul. 2008.

Omran et al., "D-Ribose improves diastolic function and quality of life in congestive heart failure patients: a prospective feasibility study," Oct. 1, 2003, *The European Journal of Heart Failure*, 5:615-19.

Omran et al., "Ribose Improves Myocardial Function and Quality of Life in Congestive Heart Failure Patients," *J. Mol. Cell Cardiol.*, Jun. 2001;33(6):A173.

Pasque et al, "Ribose-enhanced myocardial recovery following ischemia in the isolated working rat heart," *J. Thorac. Cardiovasc. Surg.*, Mar. 1982;83(3):390-398.

Pliml et al., "Effects of Ribose on Exercise-Indusced Ischaemia in Stable Coronary Artery Disease," *Lancet*, Aug. 29, 1992;340(8818):507-510.

Roger et al., "Heart Disease and Stroke Statistics—2012 Update; A Report from the American Heart Association," Jan. 3, 2012, *Circulation*, 125(1):e2-e220.

Schultis et al., "Xylitol in metabolism during stress conditions," *Medizin and Ernahrung*,1970;11(3):59-63 (English language abstract only).

Sharma et al., "D-Ribose Improves Doppler TEI Myocardial Performance Index and Maximal Exercise Capacity in Stage C Heart Failure," Abstract, 27th Annual ISHR American Section Meeting, New Orleans, LA, May 12-15, 2005, JMCC; 38(5):853.

Siri et al., "Vitamins $B_6$, $B_{12}$, and Folate: Association with Plasma Total Homocysteine and Risk of Coronary Atherosclerosis," *J. Am. Coll. Nutr.*,Oct. 1998;17(5):435-441.

Solzbach et al., "Vitamin C Improves Endothelial Dysfunction of Epicardial Coronary Arteries in Hypertensive Patients," *Circulation*, Sep. 2, 1997;96(5):1513-1519.

St. Cyr et al., "Enhanced high energy phosphate recovery with ribose infusion after global myocardial ischemia in a canine model," *J. Surg. Res.*, Feb. 1989;46(2):157-162.

Suskin et al., "Glucose and insulin abnormalities relate to functional capacity in patients with congestive heart failure," 2000, *European Heart Journal*, 21:1368-75.

Swan et al., "Insulin resistance in chronic heart failure: relation to severity and etiology of heart failure," Aug. 1997, *J Am Coll Cardiol.*, 30(2):527-32.

Tan et al., "Verapamil, Ribose and Adenine Enhance Resynthesis of Postischemic Myocardial ATP," *Life Sciences*, 1994;55(18);345-349.

Theilmeier et al., "Adhesiveness of Mononuclear Cells in Hypercholesterolemic Humans Is Normalized by Dietary L-Arginine,"*Arterioscler., Thromb., and Vasc. Biol.*, Dec. 1997;17(12):3557-3564.

Thompson et al., "Evaluation of D-Ribose Pharmacokinetics, Dose Proportionality, Food Effect, and Pharmacodynamics after Oral Solution Administration in Healthy Male and Female Subjects," Dec. 16, 2013, *The Journal of Clinical Pharmacology*, 54(5):546-54.

Tidball et al., "Mechanical loading regulates NOS expression and activity in developing and adult skeletal muscle," *Am. J. Physiol.*, Jul. 1998;275(1) (Pt 1):C260-C266.

Tullson et al., "Adenine nucleotide syntheses in exercising and endurance-trained skeletal muscle," Doc. No. 0363-6143/91, Copyright 1991, *The American Physiological Society*, C342-C347.

Tullson et al., "IMP metabolism in human skeletal muscle after exhaustive exercise," *J. Appl. Physiol.*, Jan. 1995; 78(1):146-152.

Vijay et al., "D-Ribose Improves Ventilatory Efficiency in Congestive Heart Failure Patients (NYHA Classes II-IV)," Abstract, Heart Failure Society of America, Boca Raton, FL, Sep. 18-21, 2005.

Vijay et al., "Ventilatory Efficiency Improves with D-Ribose in Congestive Heart Failure Patients," Abstract, 27th Annual ISHR American Section Meeting, New Orleans, LA, May 12-15, 2005 JMCC; 38(5):820.

Wagner et al., "Effects of oral ribose on muscle metabolism during bicycle ergometer in patients with AMP—deaminase-deficiency," *Purine and Pyrimidine Metabolism in Man VII*, Part B, Harkness et al., Eds., New York, 1991;383-385.

Zimmer et al., "Ribose accelerates the repletion of the ATP pool during recovery from reversible ischemia of the rat myocardium," *J. Mol., & Cell Cardiol.*, Sep. 1984;16(9):863-866.

Zöllner et al., "Myoadenylate Deaminase Deficiency: Successful Symptomatic Therapy by High Dose Oral Administration of Ribose," *Klin. Wochenschr.*, 1986;64:1281-1290.

International Patent Application No. PCT/US2017/014034, filed Jan. 19, 2017; International Preliminary Report on Patentability dated Aug. 16, 2018; 7 pages.

\* cited by examiner

Myocyte size

Cardiac fibrosis

USE OF RIBOSE FOR TREATMENT OF SUBJECTS HAVING CONGESTIVE HEART FAILURE

This application claims the benefit of U.S. Provisional Application No. 62/289,562, filed Feb. 1, 2016, which is herein incorporated by reference in its entirety.

BACKGROUND

In the United States, an estimated 5.8 million people, divided equally between men and women, have chronic heart failure (CHF), also known as chronic cardiac failure (CCF) or chronic congestive heart failure. Of these, almost 1.4 million are under 60 years of age. Prevalence of CHF is increasing substantially with an estimated 400,000 new cases each year according to National Heart, Lung, and Blood Institute (NHLBI) statistics. As CHF is the end stage of cardiac disease, half of the patients diagnosed with CHF will die within 5 years. Increasing prevalence, hospitalizations, and deaths have made CHF a major chronic problem in the United States and one of the most common causes of hospitalization.

CHF treatments are currently limited to alleviating symptoms of existing heart failure including, through significant life style changes, medications such as diuretics and ACE inhibitors which can have significant side effects, and surgery. All current treatments for heart disease which do not treat the inciting lesions themselves (i.e., coronary artery stents, valve replacements, etc.) are secondary in nature. Some medications, for example, will produce dilation of the vessels in the body and, therefore, reduce the resistance to blood flow which the heart must overcome. This does not treat the cardiomyocytes directly but it does reduce the work the heart must do, providing secondary benefit.

There is a continuing need for methods of treating heart failure patients to reduce the symptoms and/or to improve the cardiac function of the subject.

SUMMARY

In one aspect, the present disclosure provides methods for treating a human subject having congestive heart failure.

In one embodiment, the method includes orally administering a 10 g to 50 g dose of D-ribose daily to a subject having congestive heart failure, wherein the D-ribose is administered in a single dose after fasting, and the administration of D-ribose is continued over a period of time effective to improve cardiac and/or physical function of the subject.

In another embodiment, the method includes orally administering a 100 mg/kg to 500 mg/kg dose of D-ribose daily to a subject having congestive heart failure, wherein the D-ribose is administered in a single dose after fasting, and the administration of D-ribose is continued over a period of time effective to improve cardiac and/or physical function of the subject.

In some embodiments, the subject has fasted for at least 3 hours, 4, hours, 5 hours, 6 hours, 7 hours, 8 hours, 9 hours, 10 hours, 11 hours, 12 hours, or more. In some embodiments, the D-ribose is administered orally in the morning after overnight fasting.

In certain embodiments, the administration of D-ribose in continued over a period of time in which treatment of the congestive heart failure is desired. In some embodiments, the administration of D-ribose is continued over a period of at least two weeks, at least three weeks, at least three months, at least six months, at least one year, or longer.

In certain embodiments, the subject, prior to treatment, exhibits advanced systolic or diastolic dysfunction.

In certain embodiments, the subject, prior to treatment, exhibits acute decompensation of heart failure.

In certain embodiments, the improved physical function of the subject after treatment includes increased sub-maximal or maximal exercise capacity.

In certain embodiments, the improved physical function of the subject includes improved assessments of fatigue, dyspnea, edema, Global Clinical Status, and/or other physician or patient derived outcomes.

In certain embodiments, administering the D-ribose results in a decreased rate of myocardial remodeling or reverse myocardial remodeling including, for example, a reduction in heart size or weight and/or a reduction in ventricular diameter or volume.

In certain embodiments, administering the D-ribose results in a decreased rate of myocardial remodeling or reverse myocardial remodeling including, for example, a decreased rate of left ventricular wall thickening, posterior wall thickening, and/or interventricular wall thickening.

In certain other embodiments, the method includes: orally administering a 10 g to 50 g daily dose of D-ribose in a single dose after fasting to a subject having congestive heart failure; and orally administering one or more additional 0.01 g to 50 g doses per day of D-ribose to the subject, wherein the administration of D-ribose is continued over a period of time effective to improve cardiac and/or physical function of the subject.

In certain other embodiments, the method includes: orally administering a 100 mg/kg to 500 mg/kg daily dose of D-ribose in a single dose after fasting to a subject having congestive heart failure; and orally administering one or more additional 0.1 mg/kg to 500 mg/kg doses per day of D-ribose to the subject, wherein the administration of D-ribose is continued over a period of time effective to improve cardiac and/or physical function of the subject.

DEFINITIONS

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above brief description of various embodiments of the present invention is not intended to describe each embodiment or every implementation of the present invention. Rather, a more complete understanding of the invention will become apparent and appreciated by reference to the following description and claims. Further, it is to be understood that other embodiments may be utilized and structural changes may be made without departing from the scope of the present invention.

DETAILED DESCRIPTION OF ILLUSTRATIVE EMBODIMENTS

D-ribose is a pentose sugar that is structurally integral to important biological compounds such as adenosine triphosphate (ATP), deoxynucleotides (DNA), ribonucleotides (RNA), and all other nucleotides and nucleosides.

The parenteral administration of D-ribose to treat patients having myocardial stress has been disclosed in U.S. Pat. No. 8,710,018 B2 (Foker). Foker disclosed that the parenteral administration of D-ribose may reduce the progression to heart failure as a consequence of the cardiac stress. Foker further discloses that upon discharge, the patient may be converted to oral dosage of about 10-20 grams of ribose, typically in divided doses. Despite this disclosure, there is still a need for methods of treating patients that have developed congestive heart failure, preferably without the use of parenteral administration of D-ribose.

The use of D-ribose to supplement the diet of subjects suffering from cardiovascular or peripheral vascular disease or those at risk for such conditions has been disclosed in U.S. Pat. No. 7,553,817 B2 (Butler et al.). Butler et al. disclosed that D-ribose alone may be orally administered to a patient at least once a day in unit dosages of from two to ten grams, for example, with meals. Although improvements in cardiovascular function were reported for these doses, Butler et al. suggest that higher doses of D-ribose should be avoided to reduce the occurrence of side effects such as hypoglycemia with concomitant dizziness, nausea, and sweating, along with possible abdominal distress and diarrhea.

Pharmacokinetics for the oral administration of D-ribose to healthy male and female subjects was studied and reported by Thompson et al. (The Journal of Clinical Pharmacology, 54:546-554, 2013). Thompson et al. reported that for these healthy subjects, D-ribose is absorbed faster than it is metabolized. Although administration of D-ribose immediately following meals resulted in blood levels of D-ribose greatly reduced from those observed with administration after fasting, blood levels of D-ribose were observed to generally increase more than proportionally with increasing dose.

Figure 1:
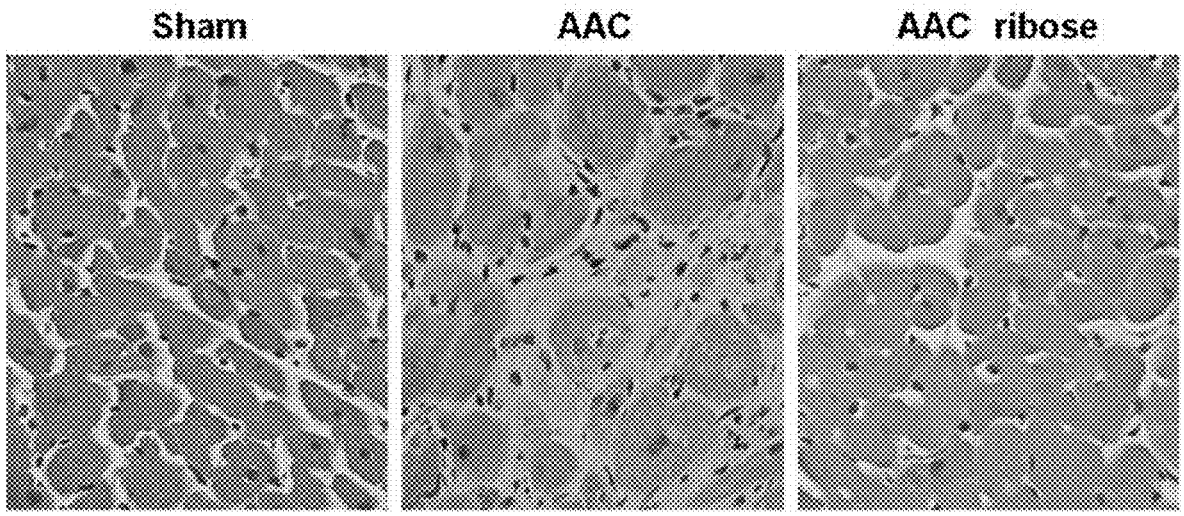
FIG. 1 is an illustration of tissue sections demonstrating mycocyte size differences between groups of mice in an exemplary mice model as disclosed herein.
Figure 2:
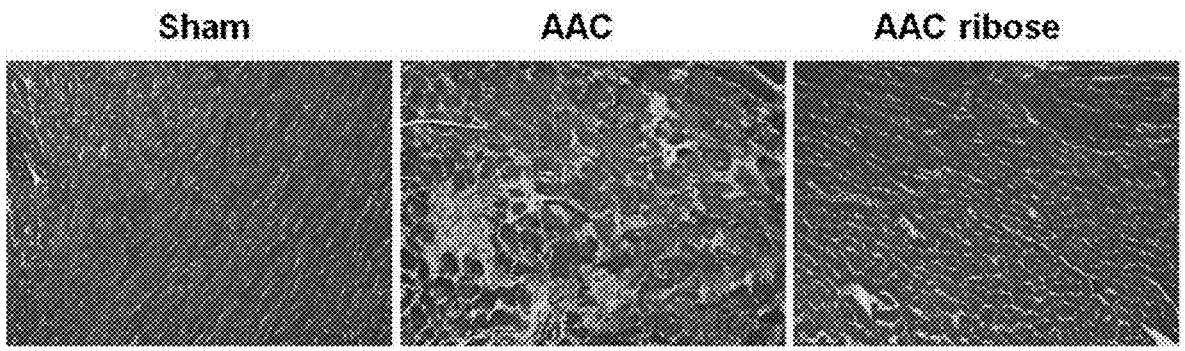
FIG. 2 is an illustration of tissue sections demonstrating differences in degree of fibrosis (light gray stain) between groups of mice in an exemplary mice model as disclosed herein.

Surprisingly, the present inventors have now found that the pharmacokinetics for the oral administration of D-ribose to subjects with stable congestive heart failure is markedly different than that observed for healthy subjects. Although a morning oral dose of D-ribose (overnight fasting) produced significant blood plasma levels, the mid-day and evening doses produced diminished blood levels similar to that observed in healthy subjects given food immediately prior to dosing, even though D-ribose administration to subjects with stable congestive heart failure occurred over 2 hours after their previous meal. However, in some cases, little or no measurable plasma concentrations of D-ribose were observed, a phenomenon that did not occur in healthy subjects. The study further suggested that for subjects with stable congestive heart failure, dosages less than 10 g may not result in therapeutic blood plasma levels of D-ribose.
Mouse Model Surprisingly, the present inventors have also observed evidence of a remodeling effect after administration of D-ribose in a mouse model of chronic pressure overload. In this model, mice treated with a once daily subcutaneous dose of D-ribose showed a significantly diminished degree of remodeling compared to untreated controls. This remodeling effect was manifested by lower left ventricular dimensions, lower ventricular wall thicknesses, and greater fractional shortening values compared to untreated controls. In addition, heart weights were greater in untreated controls than D-ribose treated animals. Furthermore, histological evaluation of these mouse hearts revealed that D-ribose treated animals had significantly smaller myocyte dimensions (FIG. 1) and a significantly lower degree of fibrosis (FIG. 2). The study consisted of two ribose treated groups (high and low dose) with the high dose treated group responding better than the low dose group compared to untreated controls. The high dose provided D-ribose exposures that were 4-fold greater than observed in the low dose group providing evidence of a dose effect. The once daily, subcutaneous administration of D-ribose was intended to mimic once daily oral dosing in humans. Subcutaneous administration can bypass the high level of metabolism that takes place in the intestine of rodents, a phenomenon that does not occur in humans. In conclusion, single daily doses of D-ribose decreased the rate of remodeling occurring in mice with chronic pressure overload and higher D-ribose doses provided a greater degree of improvement.
Canine Model It has been shown that administration of D-ribose can improve cardiac function in animal models of heart failure. These results are manifested by the increased longevity of D-ribose treated animals. Animals treated with once daily, oral D-ribose at a weight equivalent dose of 10 g in a 70 kg human lived 40% longer than placebo animals. It has been hypothesized that D-ribose helps retain cardiac function by maintaining the adenylate pool in cardiomyocytes that are overworked due to underlying heart disease. Supplemental D-ribose can bypass the cell's need to synthesize D-ribose via the pentose phosphate shunt, which can be a rate limiting step to synthesis of ATP in cardiomyocytes by either the salvage or de novo pathways. It has been shown in several studies that D-ribose can enhance the rate of recovery of ATP and other constituents of the adenylate pool in the hearts of animals subjected to hypoxic stress. However, there may be additional benefits to D-ribose treatment in subjects suffering from diminished mitochondrial function in disease states such as coronary artery disease, ischemic heart disease, dilated cardiomyopathy, or other conditions leading to heart failure.

EXAMPLES

Example 1: Myocardial Remodeling with D-Ribose Administration in a Mouse Model of Chronic Pressure Overload Mice were subjected to ascending aortic constriction (AAC) leading to LV hypertrophy followed by severe LV systolic dysfunction and associated heart failure. In this situation, mitochondrial ATP synthesis is reduced and ROS production is increased in association with advancing heart failure. Reduced ATP levels can contribute to progressive loss of cardiac function from increasing energy deficit. Increased ROS can result in oxidation of critical enzymes and a diminished reducing environment, leading to apoptosis and fibrosis, which are aspects of cardiac remodeling.

Mice were divided into four groups; Sham controls (same thoracic surgery with no constriction), AAC untreated, and AAC D-ribose treated (high and low dose). D-ribose for injection (5% to 50% weight/volume) was administered at a dose of 25 to 500 mg/kg body weight by subcutaneous or intraperitoneal injection one to four times daily. After initiation of D-ribose treatment, animals in all groups were monitored for progressive heart failure using echocardiography. LV volumes, fractional shortening, and LV wall thicknesses were measured at 10 and 15 weeks. When LV dilation and fractional shortening were sufficiently advanced, animals were subjected to physical function testing using a motorized treadmill. Animals were allowed to recover for one week and their hearts were harvested and evaluated histologically for myocyte hypertrophy and fibrosis.

Echocardiography data revealed a significantly lower degree of remodeling in high dose AAC D-ribose treated animals compared AAC controls in left ventricular dimensions ($p<0.01$ at systole and $p=0.01$ at diastole), left ventricular fractional shortening ($p<0.01$) and total wall thickness ($p<0.03$). Low dose AAC D-ribose treated mice demonstrated numerical improvements in these same parameters; however, only total wall thickness was statistically significant ($p<0.04$), suggesting these D-ribose induced effects are dose-dependent. In addition, tissue sections from high dose AAC D-ribose treated mice, compared to AAC control mice, exhibited significantly smaller myocyte diameters ($p<0.05$) and significantly less fibrosis as determined by differential staining ($p<0.05$).

Example 2: Pharmacokinetics of D-Ribose in Subjects with Chronic Heart Failure

The safety, tolerability, pharmacokinetics and pharmacodynamics of multiple oral doses of D-ribose solution was studied in 14 subjects with stable, chronic heart failure. It is well known that bolus oral D-ribose can induce a dose-dependent transient hypoglycemia that is preceeded by a transient spike in insulin levels. This can result in symptomatic hypoglycemia in subjects whose blood glucose levels fall sufficiently far. This transient hypoglycemia is the dose limiting side effect of D-ribose treatment, although it is readily overcome by drinking a glass of fruit juice. For this reason, subjects were initially administered a 10 g dose, fasted, followed 5 hours later by a 5 g dose at least 2.5 hours after the end of the previous meal. Subjects that tolerated the 10 g dose completed the remainder of the study at the 10 g dose. If subjects did not tolerate the 10 g dose but did tolerate the 5 g dose, they completed the remainder of the study at the 5 g dose. All subjects tolerated the 10 g dose, so the remainder of the study was conducted using the 10 g dose only. For the next two days, subjects were administered 10 g of D-ribose solution three times daily at 5 hour intervals beginning with a fasted morning dose around 7 a.m. Meals were served two hours after each dose such that the second and third daily doses were administered approximately 2.5 hours after completion of the previous meal. On the third day of dosing, subjects were administered a single dose of chewable tablets containing 16 g of glucose at 0, 30, and 60 minutes post-dose according to a predefined randomization schedule. The purpose of this was to determine whether glucose could attenuate any symptomatic hypoglycemia (if observed), or if it would impact the rate or extent of D-ribose absorption into the blood. Blood levels of D-ribose and insulin were determined at pre-defined time points throughout the study. Blood glucose levels were monitored continuously throughout the study. Four major outcomes emerged from this study. The 10 g bolus oral dose of D-ribose was well tolerated and there were no episodes of symptomatic hypoglycemia, even with fasted doses. Mean blood levels of D-ribose following a mid-day dose of 5 g D-ribose resulted in exposures that were 30-fold lower than the 10 g fasted morning dose. Blood levels from the mid-day and evening doses of D-ribose were roughly 40% that of a 10 g fasted morning dose, but more importantly, 30% of these non-fasted doses resulted in blood levels less than 15% of what was observed with a 10 g fasted dose. This phenomenon was not observed in normal subjects and appears unique to heart failure patients. Lastly, supplemental glucose administered between 0 and 60 minutes post-dose had no effect on D-ribose absorption into the blood.

Example 3: Increased Longevity in a Canine Model of Heart Failure Due to D-Ribose Treatment Dogs were surgically implanted with a cardiac pacing device used to induce heart failure through chronic cardiac pacing. In addition, an aortic catheter, coronary sinus catheter (for blood sampling), left ventricular catheter and pressure transducer, left ventricular piezoelectric crystals, and a transonic flow probe in the left circumflex coronary artery were implanted to measure a variety of hemodynamic parameters and to sample coronary venous blood. Subsequent to recovery from surgery, animals were paced for 3 weeks at a rate of 210 beats per minute (bpm) followed by an increased rate of 350 bpm which continued until the animals were deemed to be terminal. Hemodynamic and metabolic measurements were made on a scheduled basis throughout the pacing period. Dogs were treated with 150 mg/kg D-ribose solution orally either once daily (fasted) or three times daily. Placebo dogs were given an equivalent volume of water. D-ribose treatment started 10 days following the start of pacing and continued until the animal was deemed to be terminal. There were no significant differences in hemodynamics or other metabolic measures between D-ribose treated dogs and placebo. However, one significant difference was how long the D-ribose treated animals lived. Dogs treated once daily lived an average of 38.3 days versus 27.3 days for placebo animals ($p<0.03$). Furthermore, although the group of dogs treated three times daily (tid) with D-ribose consisted of fewer animals than the group of dogs treated once daily, the tid group lived on average 30.5 days, which was not statistically different than placebo animals ($p>0.20$). Although a hemodynamic or metabolic basis for this improvement was not observed, dogs treated once daily with an oral dose equivalent to 10 g in a 70 kg human, lived 40% longer than placebo animals.

Example 4: Functional Improvement to Patients with NYHA Class II to IV Heart Failure Taking D-Ribose Oral D-ribose powder for solution is administered at a dose of 10 to 50 grams per dose, once daily, fasted (e.g., 3 hours, 4, hours, 5 hours, 6 hours, 7 hours, 8 hours, 9 hours, 10 hours, 11 hours, 12 hours, or more). D-ribose powder for solution is dissolved in 50 to 250 mL of water or clear beverage and is consumed within a 15 to 60 minute period. It is preferred that D-ribose be administered to patients that are fasted. Patients are administered D-ribose for a period of at least two weeks, but possibly for the remainder of their lives. Within a period of 3 months to one year, in at least some embodiments, patients taking D-ribose may show improved assessments of fatigue, dyspnea, edema, Global Clinical Status, and/or other physician or patient derived outcomes compared to patients not taking D-ribose. In addition, in at least some embodiments, patients may exhibit improved sub-maximal exercise capacity that may be demonstrated by longer distances traveled in the Six Minute Walk Test or maximal exercise capacity that may be demonstrated by cardiopulmonary exercise (CPX) testing.

Example 5: Improved Remodeling Effects to Patients with NYHA Class II to IV Heart Failure Taking D-Ribose Oral D-ribose powder for solution is administered at a dose of 10 to 50 grams per dose, once daily, fasted (e.g., 3 hours, 4, hours, 5 hours, 6 hours, 7 hours, 8 hours, 9 hours, 10 hours, 11 hours, 12 hours, or more). D-ribose powder for solution is dissolved in 50 to 250 mL of water or clear beverage and consumed within a 15 to 60 minute period. It is preferred that D-ribose be administered fasted. Patients are administered D-ribose for a period of at least two weeks but possibly for the remainder of their lives. Within a period of 3 months to one year, in at least some embodiments, patients taking D-ribose may have a lower Left Ventricular Systolic Volume Index (LVESVI), a lower Left Ventricular Diastolic Volume Index (LVEDVI), higher Ejection Fractions (EF), higher $dP/dt_{max}$ values, lower $dP/dt_{min}$ values, and/or higher cardiac output than patients taking placebo.

Example 6: Improved Symptoms of Dyspnea and/or Edema in D-Ribose Treated Patients Hospitalized for Acutely Decompensated Heart Failure Patients admitted to the hospital for acute decompensated heart failure may be given oral D-ribose powder for solution at a dose of 10 to 50 grams per dose, once daily, fasted (e.g., 3 hours, 4, hours, 5 hours, 6 hours, 7 hours, 8 hours, 9 hours, 10 hours, 11 hours, 12 hours, or more). D-ribose powder for solution is dissolved in 50 to 250 mL (preferably 50 mL in this case) of water or clear beverage and consumed within a 15 to 60 minute period. It is preferred that D-ribose be administered to patients that are fasted. Patients are treated until symptoms of dyspnea and fluid overload have stabilized. At least in some embodiments, patients taking oral D-ribose solution may exhibit reduced symptoms of dyspnea within a significantly shorter timeframe than patients taking diuretics only.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for treating an adult human subject having stable congestive heart failure, comprising:
    orally administering a 10 g to 15 g dose of D-ribose daily to an adult human subject having stable congestive heart failure, wherein the D-ribose is administered in a single dose in the morning after overnight fasting for at least 6 hours, and the administration of D-ribose is continued over a period of time exceeding 3 weeks to improve cardiac function of the adult subject, physical function of the adult subject, or both cardiac and physical function of the adult subject.

2. The method of claim 1 wherein the administration of D-ribose is continued over a period of at least three months.

3. The method of claim 1, wherein the administration of D-ribose is continued over a period of at least six months.

4. The method of claim 1, wherein the administration of D-ribose is continued over a period of at least one year.

5. The method of claim 1 wherein the subject, prior to treatment, exhibits advanced systolic or diastolic dysfunction.

6. The method of claim 1 wherein the improved physical function of the subject comprises increased sub-maximal or maximal exercise capacity.

7. The method of claim 1 wherein the improved physical function of the subject comprises improved assessments selected from the group consisting of fatigue, dyspnea, edema, Global Clinical Status, other patient derived outcomes, and combinations thereof.

8. The method of claim 1 wherein administering the D-ribose results in a decreased rate of myocardial remodeling or reverse myocardial remodeling.

9. The method of claim 1 wherein administering the D-ribose provides an outcome selected from the group consisting of a reduction in heart size, a reduction in heart weight, a reduction in ventricular diameter, a reduction in ventricular volume, and combinations thereof.

10. The method claim 1 wherein administering the D-ribose provides an outcome selected from the group consisting of a decreased rate of left ventricular wall thickening, a decreased rate of posterior wall thickening, a decreased rate of interventricular wall thickening, and combinations thereof.

11. A method for treating an adult human subject having stable congestive heart failure comprising:
    orally administering to an adult human subject having stable congestive heart failure, a daily dose of D-ribose in mg/kg of the subject's body weight which is equivalent to 10 g to 15 g of D-ribose at a body weight of 70 kg, wherein the D-ribose is administered in a single dose in the morning after overnight fasting for at least 6 hours, and the administration of D-ribose is continued over a period of time exceeding 3 weeks to improve cardiac function of the adult subject, physical function of the adult subject, or both cardiac and physical function of the adult subject.

12. The method of claim 11, wherein the administration of D-ribose is continued over a period of at least three months.

13. The method of claim 11, wherein the administration of D-ribose is continued over a period of at least six months.

14. The method of claim 11, wherein the administration of D-ribose is continued over a period of at least one year.

15. The method of claim 11, wherein the subject, prior to treatment, exhibits advanced systolic or diastolic dysfunction.

16. The method of claim 11, wherein the improved physical function of the subject comprises increased sub-maximal or maximal exercise capacity.

17. The method of claim 11, wherein the improved physical function of the subject comprises improved assessments selected from the group consisting of fatigue, dyspnea, edema, Global Clinical Status, other patient derived outcomes, and combinations thereof.

18. The method of claim 11, wherein administering the D-ribose results in a decreased rate of myocardial remodeling or reverse myocardial remodeling.

19. The method of claim 11, wherein administering the D-ribose provides an outcome selected from the group consisting of a reduction in heart size, a reduction in heart weight, a reduction in ventricular diameter, a reduction in ventricular volume, and combinations thereof.

20. The method claim 11, wherein administering the D-ribose provides an outcome selected from the group consisting of a decreased rate of left ventricular wall thickening, a decreased rate of posterior wall thickening, a decreased rate of interventricular wall thickening, and combinations thereof.

* * * * *